United States Patent [19]
Salahieh et al.

[11] Patent Number: 5,769,870
[45] Date of Patent: Jun. 23, 1998

[54] PERFUSION DEVICE FOR MAINTAINING BLOOD FLOW IN A VESSEL WHILE ISOLATING AN ANASTOMOSIS

[75] Inventors: Amr Salahieh, Campbell; Charles S. Taylor, San Francisco; Alfredo R. Cantu, Fremont; Ivan Sepetka, Los Altos, all of Calif.; Robert G. Matheny, Carmel, Ind.

[73] Assignee: Cardiothoracic Systems, Inc., Cupertino, Calif.

[21] Appl. No.: 603,415

[22] Filed: Feb. 20, 1996

[51] Int. Cl.$^6$ ............................................. A61M 29/00
[52] U.S. Cl. ...................... 606/198; 606/108; 606/153; 606/194; 606/192; 623/1; 623/12
[58] Field of Search ............................ 606/108, 153, 606/191, 192, 194, 198; 623/1, 12

[56] References Cited

U.S. PATENT DOCUMENTS

| | | |
|---|---|---|
| 4,168,708 | 9/1979 | Lepley, Jr. et al. . |
| 4,230,119 | 10/1980 | Blum . |
| 4,483,339 | 11/1984 | Gillis . |
| 5,034,001 | 7/1991 | Garrison et al. . |
| 5,036,868 | 8/1991 | Berggren et al. . |
| 5,071,407 | 12/1991 | Termin et al. . |
| 5,087,247 | 2/1992 | Horn et al. . |
| 5,192,289 | 3/1993 | Jessen ..................................... 606/153 |
| 5,242,399 | 9/1993 | Lau et al. . |
| 5,323,789 | 6/1994 | Berggren et al. . |
| 5,328,471 | 7/1994 | Slepian . |
| 5,368,566 | 11/1994 | Crocker . |
| 5,395,333 | 3/1995 | Brill . |
| 5,397,307 | 3/1995 | Goodin . |
| 5,403,280 | 4/1995 | Wang . |
| 5,449,372 | 9/1995 | Schmaltz et al. . |
| 5,484,412 | 1/1996 | Pierpont . |
| 5,522,882 | 6/1996 | Gaterud et al. ........................ 606/108 |
| 5,645,560 | 7/1997 | Crocker et al. ........................ 606/108 |

FOREIGN PATENT DOCUMENTS 0 327 325  1/1989  European Pat. Off. .

WO 97/10753  3/1997  WIPO .

OTHER PUBLICATIONS

"Intraluminal Bypass Device for Arterial Surgery," DS Feldman, JF Hunger and SL Hale *Journal of Investigative Surgery*, vol. 3, pp. 169–176.

"Internal Vessel Occlusion: An Improved Technique for Small Vessel Anastomosis," JB Griffin, M.D. and RL Meng, M.D. *J. Vasc. Surg.*, 1986; vol. 4, pp. 616–618.

Research Medical Vascular Product Brochure entitled "Balloon, Tapered and Straight Carotid Artery Shunts. A Complete Line for Every Surgeon's Preference." (4 pgs).

(List continued on next page.)

*Primary Examiner*—Michael Buiz
*Assistant Examiner*—Daphna Shai
*Attorney, Agent, or Firm*—Lyon & Lyon LLP

[57] ABSTRACT

A plurality of embodiments of a distal perfusion device are disclosed, which device facilitates anastomosis constructions by maintaining a dry anastomosis site while simultaneously maintaining blood flow distally in the blood vessel to prevent ischemia and reduce overall patient trauma. The perfusion device is configured for installation into a blood vessel such as a left anterior descending coronary artery through an incision therein, to which is to be grafted a distal end of a blood vessel such as an internal mammary artery. The device includes a central member of selected configuration and material, terminating at either end thereof in respective selectively tapered end members. A lumen extending through the central member and end members, and selected perforations in the end members, maintain blood flow through the perfusion device. A selected portion or portions of the device's outer circumference fit snugly within the artery in the regions beyond and/or at the anastomosis site, to maintain the latter free of blood. Several methods for deploying and removing respective embodiments of the device also are illustrated.

22 Claims, 10 Drawing Sheets

OTHER PUBLICATIONS

"Reduced Incidence of Intraoperative Myocardial Infarction During Coronary Bypass Surgery with Use of Intracoronary Shunt Technique," AJ Franzone, E Wallsh, SH Stertzer, NP DePasquale, and MS Bruno *The American Journal of Cardiology*, vol. 39, Jun. 1977, pp. 1017–1020.

"Placement of Coronary Artery Bypass Graft Without Pump Oxygenator," WG Trapp and R Bisarya *The Annals of Thoracic Surgery*, vol. 19, No. 1, Jan. 1975.

"Technique for Using Soft, Flexible Catheter Stents in Aortocoronary Vein Bypass Operations," LG Ludington, G Kafrouni, MH Peterson, JJ VErska, A Mulder, and LA Brewer Department of Thoracic and Cardiovascular Surgery, White Memorial Center, Los Angeles, CA, pgs. (Jun. 25, 1975) pp. 328–332.

"Minimally Invasive Coronary Bypass Surgery with Internal Thoracic Artery Grafting: Early Experience and Critical Analysis," SA Oliveira, JM Souza, S Rogas, LA Dallan, LA Lisboa Hospital Beneficiencia Protuguesa –Sao Paulo –Brazil, p. 44.

"Mammary Artery–Coronary Artery Anastomosis as Method of Treatment for Angina Pectoris," V.I. Kolesov, M.D. *Thoracic and Cardiovascular Surgery*, vol. 54, No. 4, Oct., 1967, pp. 535–544.

"Coronary Artery Grafting Without Heart Lung Bypass Using A Temporary Intracoronary Shunt," MM Levinson, G Fooks, and LR Sauvage *The Heart Surgery Forum*, Apr. 22, 1995, pp. 1–7.

"Use of the Doubly Tapered Graft for the Creation of a Systemic–Pulmonary Arterial Shunt," NS Braunwald and AR Castaneda *The Annals of Thoracic Surgery*, vol. 22, No. 3, Sep. 1976, pp. 239–244.

PERFUSION DEVICE FOR MAINTAINING BLOOD FLOW IN A VESSEL WHILE ISOLATING AN ANASTOMOSIS

BACKGROUND OF THE INVENTION

The present invention relates to minimally invasive coronary artery bypass grafting (CABG) procedures and in particular to perfusion device for use in performing minimally-invasive microsurgeries such as internal mammary artery (IMA) or vein graft to coronary artery surgery procedures while maintaining blood flow distally in the LAD during the construction of the anastomosis, to prevent ischemia while further maintaining a dry anastomosis site to facilitate the surgery procedure.

Surgeons constantly are striving to develop advanced surgical techniques resulting in turn in the need for developing advanced surgical devices and instruments required for the performance of such techniques. Recent advances in the surgical field increasingly are related to operative techniques which involve less invasive surgical procedures and reduce overall patient trauma. To illustrate, in the field of CABG procedures it has been common practice for surgeons to perform a sternotomy to expose the body cavity in the thorax region, wherein retractors are employed to provide the surgeons the access required to perform the necessary bypass surgery.

However, more recent surgical techniques employ less invasive CABG procedures known as endoscopic surgery involving the use of an endoscope instrument which permits the visual inspection and magnification of any cavity in the body, such as the thorax cavity. The procedure involves the insertion of tubes called a trocar cannulas through the soft tissue protecting the body cavity. The surgeon then performs diagnostic and therapeutic procedures at the surgical site with the aid of specialized micro-instrumentation designed to fit through the various trocar cannulas that provide the required openings into the body cavity.

In such endoscopic techniques, an arterial blood source such as the IMA is dissected from its location, transected and prepared for attachment at an anastomosis site on a selected coronary artery, commonly the LAD. To this end, a portion of the LAD is exposed and an incision is made in the arterial wall. The distal end of the IMA is then sutured over the incision in the LAD to conclude the bypass graft surgery.

However, in order to perform the above surgical procedures, heart activity must be arrested. Thus, to maintain the patient, it is necessary first to divert the patient's blood circulation through an extracorporeal cardiopulmonary bypass system. This is accomplished by isolating the heart at selected arterial locations using selected catheter instruments and occluders to draw the blood into the bypass system for oxygenation thereof via an associated pump oxygenator. The oxygenated blood is returned to the patient to maintain the patient's systemic circulation during the surgery. The procedure further includes the ligating of vessels by pinching off the vessel with sutures and/or the use of occluder devices in the artery, the functions of which are to prevent the flow of blood through the artery to maintain a dry surgical site during the suturing of the anastomosis.

Accordingly, typical cardiovascular surgical procedures such as that of previous mention include the procedures of placing the patient on a cardiopulmonary bypass system and then inducing cardioplegic arrest of the heart in situ in the patient's body. It follows that the entire anastomosis construction is performed with the heart in the arrested state, and with special precautions taken to prevent any blood flow in the vessel on which the anastomosis surgery is being performed. To this end, an occluder device which is sometimes inserted in the blood vessel to isolate the anastomosis site is specifically configured to be impenetrable to thereby prevent the flow of blood through the occluder device at the anastomosis site.

The surgical procedures of previous mention experience the disadvantages of increased trauma to the arteries caused by ligatures, to the heart due to the cessation of blood flow to distal portions thereof, and to the patient in general due to the cardiopulmonary bypass and cardioplegic arrest procedures and instruments. Accordingly, it would be highly desirable when performing a bypass surgery to circumvent the problems of previous mention, that is, to obviate the need for a cardiopulmonary bypass procedure and to allow the anastomosis construction to be performed without the occlusion of blood flow through the associated blood vessel, to prevent ischemia while still maintaining a dry anastomosis site to facilitate the suturing procedure.

SUMMARY OF THE INVENTION

The present invention participates in overcoming the problems of previous mention by enabling a surgeon to perform an anastomosis construction on, for example a left anterior descending coronary artery (LAD) without occluding the distal flow of blood through the LAD to the heart. The invention thus facilitates the anastomosis construction by keeping the surgical site free of blood while preventing ischemia and reducing overall patient trauma.

Although the present invention is described herein in the performance of anastomosis surgery involving a graft of an internal mammary artery (IMA) to a LAD, it is to be understood that the invention and associated techniques are equally applicable to performing anastomosis constructions or surgical grafts on body vessels other than the LAD-IMA employed herein for purposes of description.

The present invention comprises a distal perfusion device, hereinafter termed a "shunt" for ease of description, for use in LAD-IMA surgical procedures and the like. The shunt maintains blood flow in the LAD to prevent ischemia while maintaining a dry or blood free anastomosis site to facilitate a surgeon's suturing procedure. A shunt also provides support within the LAD if the LAD is ligated via sutures bordering the anastomosis site thereby decreasing trauma to the vessel. The shunt further may be configured with flanges, protruding edges, etc., to help expose the anastomosis to aid the positioning of a needle or otherwise further facilitate the suturing procedure.

To this end, the invention provides a microsurgical device, herein referred to as a shunt, including a generally cylindrical central portion or member formed of a thin-walled tube-like flexible material which includes a lumen therein to allow the flow of blood or other fluids through the central member. In preferred embodiments, selectively tapered end members are provided on either extremity of the central member, which extremities may be termed the proximal and distal extremities upon insertion in the LAD. The tapered end members include various configurations and perforations in the conical walls and/or in the apexes as well, as necessary to maintain the nominal blood flow through the shunt. The opposing tapered ends configuration facilitates the insertion of the shunt into an incision in the LAD by a surgeon using forceps. Since the shunt must be longer than the incision, that is, the anastomosis site, various shunts are installed in preferred embodiment by first inserting one end, generally of either end of the shunt, into the incision until the opposite end of the shunt clears its respective apex of the incision. The shunt is pressed into full coaxial alignment with the LAD and then is slid in the direction of the opposite end until it is centered within the LAD relative to the anastomosis site. A surgical thread or other filamentary strand is attached to the shunt at a strategic point or points to aid in the selected insertion of the shunt through the incision and into position in the LAD, as well as to aid in the selected removal of the shunt prior to conclusion of the anastomosis construction.

The central member and tapered end members may be integrally formed as by a molding process, or the end members may be individually formed and then coaxially affixed permanently to the extremities of the central member by a suitable bonding, gluing, etc., process. A number of materials are contemplated for use in accordance with the invention, wherein the material used, in part or in total, dictates the structural configuration of the shunt and the associated manner of inserting, expanding and/or contracting the particular shunt.

In preferred embodiments, the shunt may include spaced apart annular ridges located generally about the extremities of the central member to provide enlarged diameters for the shunt beyond either extremity of the anastomosis site to enhance the occlusion of blood therefrom. The ridges may be integrally formed about the central member or may comprise expandable members whose diameters are enlarged radially outward when required, generally upon insertion of the shunt in the LAD. Depending upon the material and associated structure, the expandable ridges may, or may not, subsequently be contractible to their initial diameters to facilitate the removal of the shunt.

In addition, a single ridge of an axial length sufficient to span the anastomosis site may be provided concentrically about the central member. The single ridge configuration preferably is an expandable member which initially is in a contracted condition to facilitate insertion. The expandable member further subsequently may be contracted to facilitate removal from the LAD.

In further embodiments, the central member itself, along with the tapered end members to a lesser extent, is selectively expandable radially outward, whereby essentially a major portion of the shunt is expanded in diameter upon demand when the shunt is in place, to occlude blood from the thusly isolated anastomosis site. As in the case of the single and dual ridge embodiments of previous discussion, the material used in forming the shunt may dictate the structure of the shunt as well as its associated manner of contraction and/or expansion.

To illustrate, in the dual or single ridge shunt configuration, the ridges may be formed of a hydrophilic polymer material which expands upon being converted to a hydrogel material in the presence of aqueous fluids. The hydrogel will undergo hydration-dehydration cycles, however since the shunt is in a wet environment the material and thus the expanded ridges may not be contractible subsequently. In an alternative embodiment the ridges may be formed of annular balloons which are both expandable and contractible on demand. The single ridge configuration is provided with a partial cylindrical sheath in the region of the anastomosis to prevent puncture of the balloon by a suture needle.

In further embodiments, the central member and the tapered end members themselves are formed of the hydrophilic material which converts to a hydrogel material when wet. Alternatively, the central member is formed of an elongated annular balloon which when expanded still provides the lumen therethrough. In another embodiment, the central member is formed of a cylindrical unfolding spiral of a polymer material which loses a sticky property and expands to a desired diameter of, for example, from 1 to 6 millimeters (mm), upon being exposed to an aqueous fluid. Such a material and the shunt generally is not contractible after expansion.

In a further alternative embodiment, the cylindrical unfolding spiral is formed of two bonded sheets of for example a nickel-titanium alloy material having an inherent shape-memory property. One sheet is annealed in the shape of a tightly curled cylinder, while the other sheet is annealed as a flat or less curled sheet. A heating coil is bonded to each sheet. The shunt is formed of the bonded sheets rolled into a spiral cylinder of selected diameter. The application of a small electrical current to one coil causes the shunt to contract, while the application of a small electrical current to the other coil causes the cylindrical spiral to unfold and expand to the desired diameter.

In still a further alternative embodiment, the shunt is formed of a cylindrical braided material of selected nominal diameter. The braided material decreases in diameter relative to the nominal diameter when stretched axially, and increases in diameter relative to the nominal when compressed axially. The shunt is formed of the braided material to define a central member with tapered end members integrally formed therewith. A selected length of the central member is impregnated with an elastomer material such as silicon, latex, etc., which is impervious to fluids while still allowing axial and radial flexibility. A thread or other filamentary strand, is attached internally to either tapered end of the shunt, whereby applying a pulling force to the thread causes the braid to contract and expand, while relaxing the pulling force allows the braided material to relax and contract.

In other alternative embodiments, various configurations of flexible springs and/or coils are employed as the basic expandable and contractible structures. The coils generally are provided with a laminated coating of, for example, a flexible elastomer material to provide the fluid impervious central member required to isolate the anastomosis site. In some embodiments the shunt diameter is controlled by the application of a force to a thread, thin wire, etc., which force in turn alters a natural state of the coil to produce an expansion and/or contraction.

In a modification of the various shunt embodiments, a portion is removed from the central member to define a necked-down mid section. This embodiment lends itself to an insertion procedure wherein the shunt is folded at the necked-down mid section via forceps or other insertion instruments and both tapered ends are inserted through an arteriotomy whereupon the shunt is gently unfolded into place in the artery.

In a further alternative embodiment, a shunt access member in the general shape of a tube, is formed in the central member of the shunt to extend generally radially therefrom. The tube includes a lumen therethrough which is in communication with the lumen of the shunt. Such an access member may provide support for the distal end of an IMA to facilitate the anastomosis construction and/or to maintain blood flow from the IMA to the artery. Further, the access member provides access to the artery by an introducer implemented in another insertion procedure particularly applicable to such a shunt configuration.

DESCRIPTION OF THE PREFERRED EMBODIMENTS

As may be seen from the following description and accompanying drawings, the present invention contemplates several basic shunt configurations, with a plurality of modifications to the configurations, wherein the modifications for the most part are interchangeably useable in the various basic shunt configurations. Likewise, while several materials particularly are of use with respective shunt configurations, several of the materials discussed herein may be used with several of the shunt configurations, as further described below. In the description of the several figures, like elements in the figures are identified by like numerals.

Figure 1:
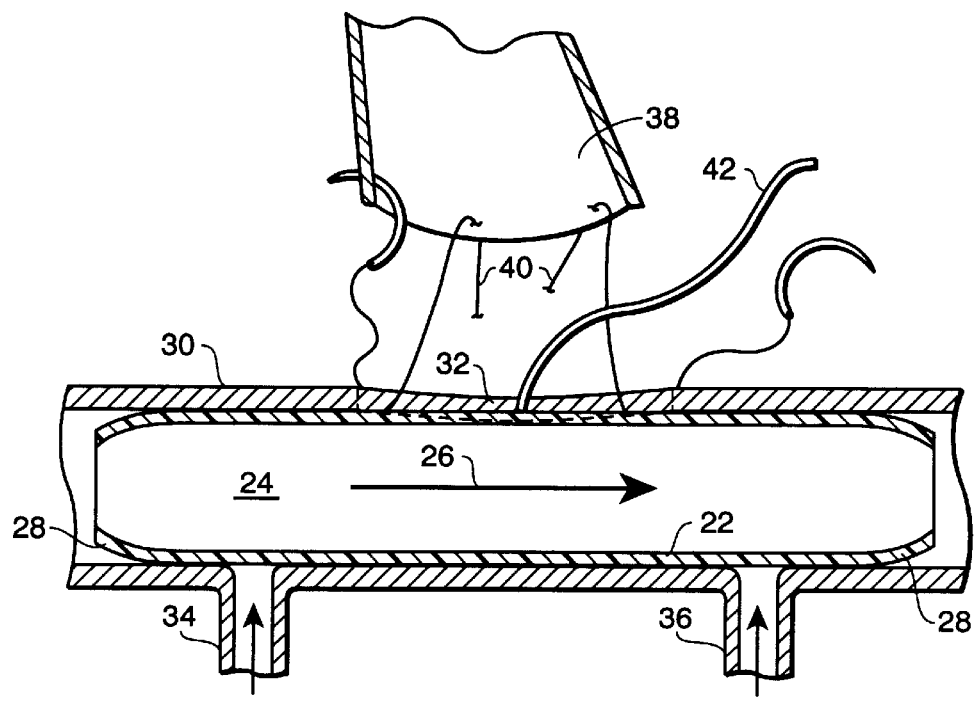
FIGS. 1 and 2 are elevational views, in cross-section, of a small segment of an artery depicting a shunt installed within the artery in accordance with the invention to isolate an anastomosis site while maintaining blood flow distally.

FIG. 1 illustrates a basic shunt 20 formed of a central member 22 having a lumen 24 therethrough for passage of blood through the shunt 20 as depicted by arrow 26. The central member 22 terminates in extremities 28 and is formed of a material such as polyurethane, polyethylene, silicon, etc. The shunt 20 is shown in FIG. 1 installed in place within, for example, a LAD artery 30 of previous mention, and particularly spanning an arteriotomy or incision 32 in the LAD which forms a site for an anastomosis construction. The shunt 20 is of sufficient outside diameter that, when installed, fits snugly within the interior walls of the LAD 30 to thereby maintain the anastomosis site, corresponding to the incision 32, free from blood while allowing blood flow 26 through the LAD. As depicted, the shunt 20 not only occludes the blood from the LAD, but also occludes blood flow from possible arterial side-branches such as depicted at 34, 36.

As is well known, the anastomosis surgery consists of grafting a distal end of, for example, the internal mammary artery (IMA) 38, to the LAD 30 to encompass the incision 32. The anastomosis is performed by the surgeon by sequentially passing sutures 40 through the edges of the incision 32 and through the distal end of the IMA 38 until suture loops are made around the confronting circumference, in conventional fashion. Prior to the suture loops being tightened to secure the graft, the shunt 20 is carefully removed from within the LAD by pulling on a thread or like filamentary strand 42 secured to a selected point on the shunt, while guiding the shunt via forceps or tweezers through the incision and adjacent loops of the sutures 40. The loops then are drawn tight to provide a fluidly sealed anastomosis.

By way of example, an arteriotomy is of the order of 5 to 12 millimeters (mm) and the perfusion devices generally are of the order of 8 to 30 mm in length, which an inside diameter from 0.5 to 4 mm and the outside diameter from 1 to 5 mm.

Figure 2:
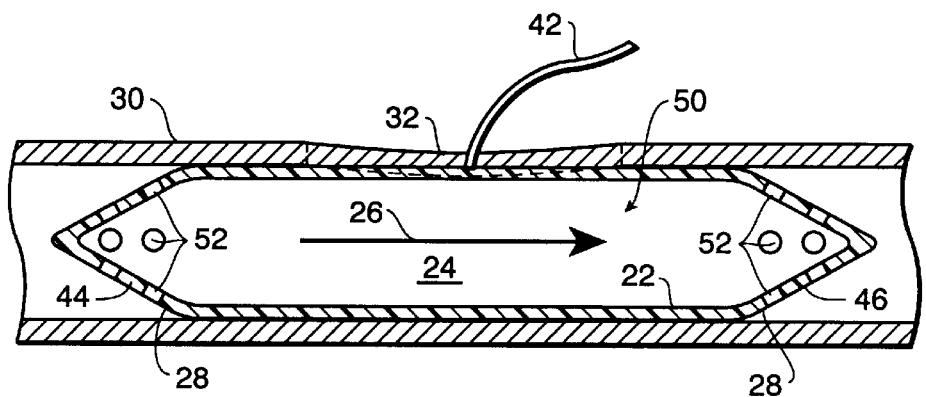

FIG. 2 depicts a modification to the shunt 20 of FIG. 1, namely the addition of more pronounced tapered end members 44, 46 to the extremities 28 of the central member 22, to form a generally symmetrically tapered shunt 50. The end members are formed of the same material as the central member 22, or may be formed separately of a material of different stiffness and then bonded, glued, etc., to the central member. The taper angle of the end members 44, 46 may vary from a slight taper with a relatively large apex opening such as in FIG. 1, to a sharp taper extending to a closed apex as in FIG. 2 or to the open apex of FIG. 1. The tapered end members 44, 46 are provided with a selected array of perforations 52, the number and arrangement of which are variable to provide the nominal blood flow.

Figure 3:
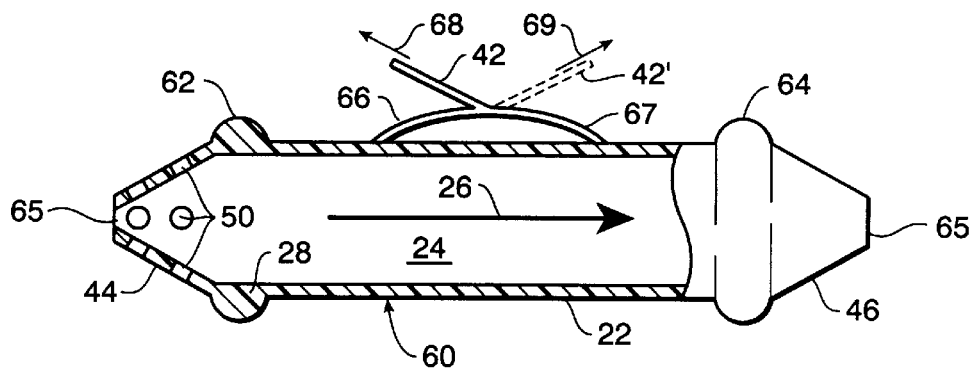
FIGS. 3, 4 and 6 are elevational views, in cross-section, of alternative embodiments of the present invention depicting additional configurations and modifications of the invention of FIGS. 1, 2.

FIG. 3 depicts an alternative embodiment of the invention wherein the shunt 50 of FIG. 2 is modified to provide a shunt 60 having annular ridges 62, 64 formed about generally the extremities 28 of the central member 22. The ridges may be formed of the same material as is the central and tapered end members 22, 44, 46 and as such are formed with pre-selected diameters. Alternatively, the ridges may be formed of other materials and/or of devices which are expandable as well as contractible as further described below in alternative embodiments. To illustrate, the annular ridges 62, 64 may be formed of the hydrophilic polymer material which, due to its disposition about the extremities 28 of the central member 22, expands radially outward as it converts to a hydrogel material upon being inserted in the aqueous fluid environment of the LAD. Other triggerable expanding polymer materials may be used as well such as open cell foam, etc. The enlarged ridges provide enhanced contact with the interior wall of the LAD to maximize the isolation of the anastomosis site. Note that the apexes of the tapered end members 44, 46 herein are depicted open at 65 to allow added blood flow, if desired. In FIG. 3, the filamentary strand 42 is attached at two spaced apart points of the central member 22 via diverging strands 66, 67. Such a dual-point strand configuration aids in the shunt insertion process, particularly when the surgeon initially inserts, for example, the end member 44 into the incision (32, FIGS. 1, 2) by pulling gently on the combined strands 42, 67 as depicted by arrow 68 toward the proximal end of the shunt 60 while urging the shunt with forceps. Once the distal end member 46 clears the incision, the shunt 60 is urged distally in the LAD with forceps and by pulling gently on the combined strands 42', 66 as depicted by arrow 69. Such a dual-point filamentary strand connection may be employed in other shunt embodiments described herein if desired.

Figure 4:
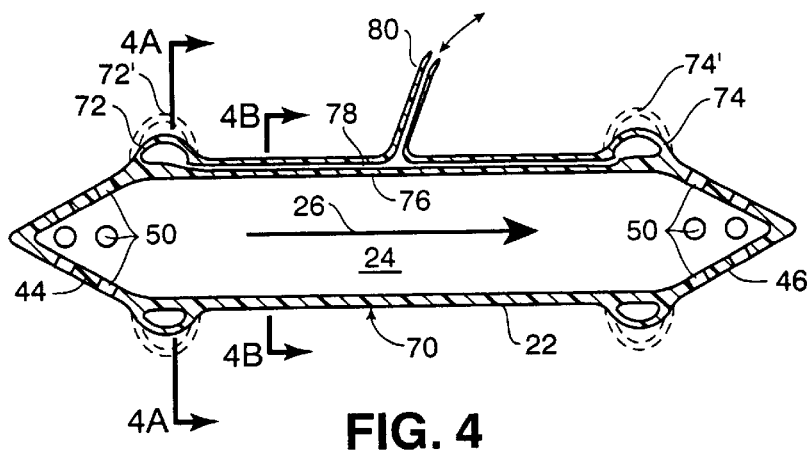

FIG. 4 depicts a shunt 70 similar in configuration to the shunt 60 of FIG. 3 but including the modification comprising selectively expandable dual ridges defined by expandable "balloons" 72, 74 which herein are integrally formed with the central and tapered end members 22, 44, 46 as shown. However, the expandable dual ridges may be provided as a separately formed assembly coaxially assembled about generally the central member, as further described in FIG. 5. As shown further in FIGS. 4A, 4B, the central member 22 includes an axially extending thickened upper section 76 within which is formed a lumen 78 which extends the length of the central member to open into respective chambers of the expandable balloons 72, 74. The lumen 78 is depicted in communication with a centrally located fluid supply tube 80 through which air, saline fluid, etc., may be supplied on demand to the balloons 72, 74 to expand them radially outward to desired diameters 72', 74', shown in phantom line. As may be seen, the dual balloons may be contracted to a reduced diameter on demand by removing the supply of fluid, or by applying a selected source of vacuum. If a centrally located supply tube such as tube 80 is used to supply the fluid on demand to the expandable balloons 72, 74, it is preferable to form the balloons of a non-compliant material, that is, a material which expands to a limit and expands no further even with the introduction of additional pressure. The use of a compliant material, such as silicon or latex, with a single supply tube could result in the expansion of one balloon but not of the other. However, a compliant material may be used if the central lumen 78 is omitted and two supply tubes supply the expansion fluid directly to respective expandable balloons 72, 74.

Figure 5:
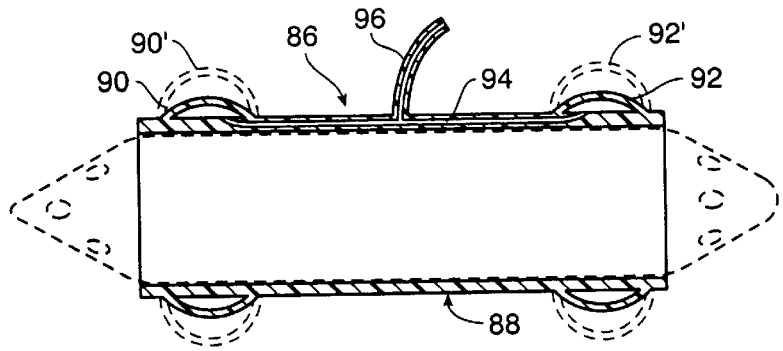
FIG. 5 is an elevational view, in cross-section, of a dual balloon configuration such as employed in the shunt embodiment of FIG. 4, illustrating one construction thereof and the manner of assembly about a shunt central member.

FIG. 5 depicts an alternative construction for providing the expandable dual balloon configuration illustrated in FIG. 4. The configuration of FIG. 5 is a separate dual balloon assembly 86 in the form of a tube-like structure which can be coaxially slid over a pre-formed shunt, such as shunts 20 and 50 of FIGS. 1 and 2, and bonded, glued, etc., to the exterior cylindrical wall of the shunt (shown herein in phantom line). The assembly 86 is formed of a central member 88 of a selected material such as polyethylene, polyurethane, polyester, etc. Expandable balloons 90, 92 formed of the same or a different material are bonded, glued, molded, etc., to respective ends of the central member 88 to define a unitary tube-like structure. An upper axial portion of the cross-section of the central member is thickened to allow the formation therethrough of a lumen 94 which communicates with respective chambers of the balloons 90, 92. A fluid supply tube 96 is formed in communication with the lumen 94 to supply or extract the air or other expansion fluid to the balloons 90, 92 on demand. In their expanded condition, the balloons 90, 92 expand radially outward to a desired diameter 90', 92', depicted in phantom line. In the example of FIG. 5, the sealed chambers of the balloons 90, 92 are formed after the assembly 86 is sealed to a shunt, however the balloons may be formed with respective internal cylindrical walls to define a totally sealed chambers/balloons assembly 86 prior to assembly about a shunt.

Figure 4A:
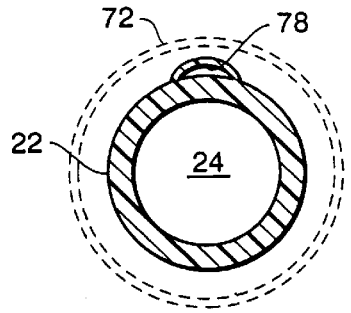
FIGS. 4A and 4B are cross-sectional views taken along section lines 4A and 4B respectively, of FIG. 4.
Figure 4B:
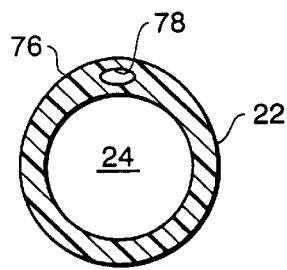

As may be seen, the configuration of the balloons 90, 92, lumen 94 and supply tube 96 resemble the configuration of the equivalent elements of FIGS. 4, 4A, 4B. As discussed previously relative to FIG. 4, the material used to form the balloons 90, 92 may be non-compliant or compliant with one or two supply tubes 96, respectively, coupled thereto.

Figure 6:
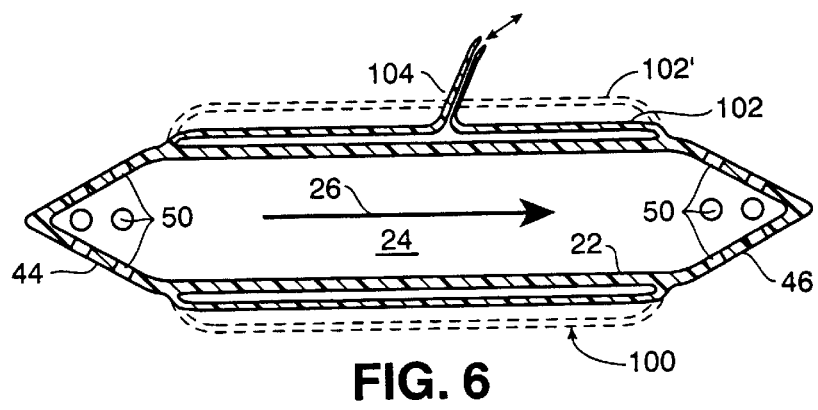

FIG. 6 depicts a shunt 100 generally formed in the manner of the FIG. 4 shunt 70, wherein however the spaced-apart dual balloon configuration is replaced with a single axially extending cylindrical balloon 102 annularly formed about the exterior cylindrical wall of generally the central member 22. A fluid supply tube 104 (or tubes) is formed in communication with an annular chamber formed by the single balloon 102 and the central member exterior wall, to supply or extract the fluid to respectively expand or contract the balloon on demand. The expanded balloon is depicted in phantom line at 102'. As previously discussed relative to FIGS. 5 and 4, the single balloon 102 configuration may be formed as a separate single balloon assembly in the form of a tube-like structure which can be coaxially slid over a pre-formed shunt and bonded, glued, etc., thereto to define the balloon chamber.

Figure 7:
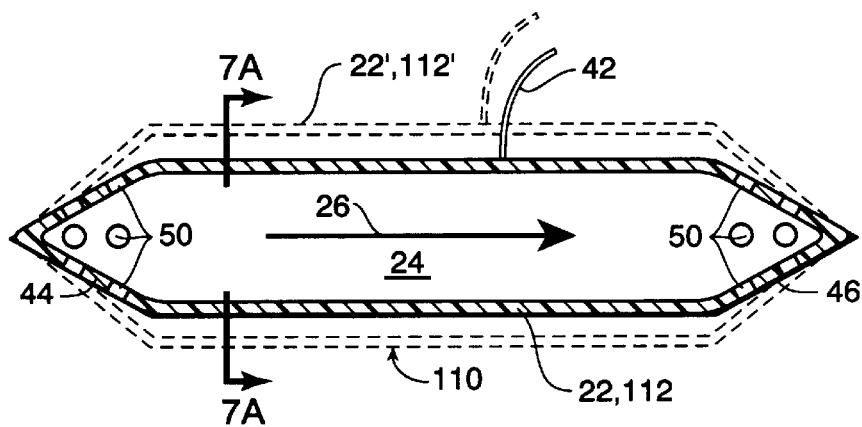
FIG. 7 is an elevational view, in cross-section, of still a further alternative embodiment of the present invention wherein the central member and tapered ends of the shunt are contractible and expandable.
Figure 7A:
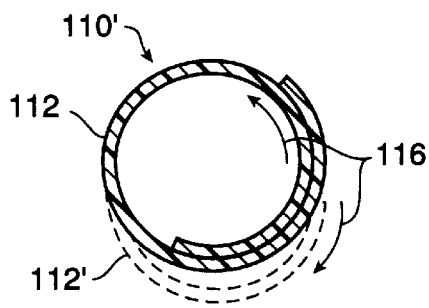
FIG. 7A is a cross-sectional view taken along section line 7A of FIG. 7.

FIG. 7 depicts another embodiment of the invention comprising a shunt 110 formed of a material which is suitably expandable upon demand in response to an inherent property and a stimulus which energizes such property. In this embodiment, the central member and, to some extent, the end members themselves expand to fit snugly within the artery. Such a material may include, for example, the hydrophilic polymer of previous discussion which expands in its hydrogel state, a material having an inherent shape-memory property such as a nickel-titanium alloy, etc. The shunt 110 may comprise the previously described configuration of a cylindrical central member 22, terminated at either extremity with tapered end members 44, 46. Alternatively, the central member may be formed not in a continuous cylinder, but may instead define a central member 112 formed of a sheet of suitable material such as polyethylene, polyurethane, polyester, etc., rolled into a cylindrical spiral with overlapping edges 114 of the sheet, as depicted in cross-section in FIG. 7A. In the spiral cylindrical configuration, the tapered end members preferably are formed to, or of, the extremities of the central member 112, and likewise may have overlapping edges.

In the expandable cylindrical configuration of FIG. 7, the shunt walls expand radially outward to increase the overall diameter of the shunt on demand such as, for example, after the shunt has been installed in place in the LAD. Depending upon the material, the cylindrical central member 112 may, or may not, be contractible radially inward when removal of the shunt is desired. In the cylindrical spiral configuration of FIG. 7A, the polymer material becomes slippery in the presence of fluids which causes the spiral of material to uncoil as depicted by arrows 116, thereby increasing the overall diameter of the shunt 110 as depicted in phantom line at 112'.

Figure 7B:
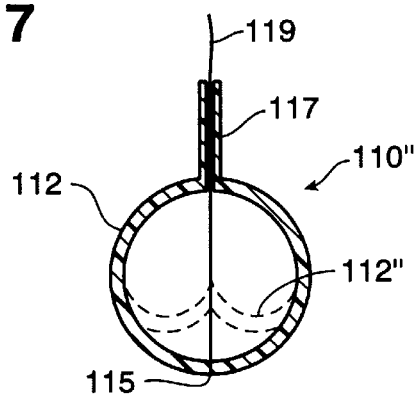
FIG. 7B is a cross-sectional view of an alternative configuration for the shunt of FIG. 7 employing a folding central member.

FIG. 7B depicts an alternative configuration for providing a contractible/expandable shunt 110" employing a polymer material and a wire 115 embedded in the central member 112 along its length. A choker tube 117 is attached to a mid point of the member 112 diametrically opposite to a mid point of the wire 115. A thread 119 attached to the wire mid point extends through the choker tube 117. The application of a pulling force on the thread 119 while holding the tube 117, causes the bottom length of the shunt to fold in as depicted in phantom line at 112Æ. This decreases the cross-section of the shunt to facilitate insertion.

Figure 8:
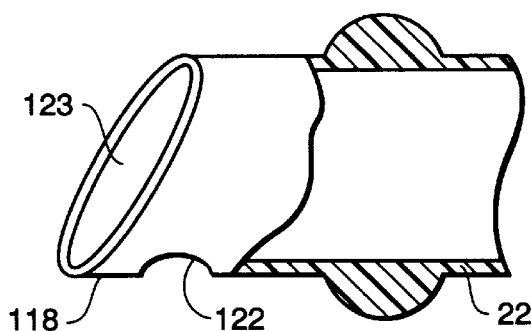
FIGS. 8 and 9 are partial elevational views, generally in cross-section, of alternative tapered end configurations which may be used in the shunts described herein.
Figure 9:
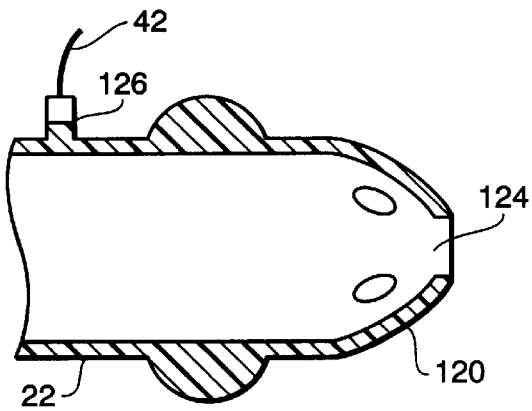

FIGS. 8 and 9 depict alternative tapered end members 118, 120, respectively, which may be used with the shunts described herein in place of the more pointed end members 44, 46 of previous description. The end member 118 is sliced preferably at an angle of the order of from 30 to 60 degrees relative to the axial length of the central member 22, and a perforation or opening 122 of selected size may be formed in the wall of the end member generally coincident with the extended point of the end member 118. The resulting tapered end of the end member 118 may be formed to curl radially inward around the oval circumference thereof to provide a more rounded end while further decreasing the size of a central opening 123.

The tapered end member 120 of FIG. 9 is shortened in length with a relatively acute taper and a central opening 124. The shortened end member 120 facilitates insertion of a shunt in an incision where the opposite end of the shunt is inserted initially, since the shortened end member 120 more readily clears the respective end of the incision. The FIG. 9 further depicts an integral stub 126 formed of the shunt material at a location approaching an extremity of the central member 22. The stub 126 provides a readily grasped portion of the shunt to facilitate the insertion of the shunt via forceps. The stub may include connection for the filamentary strand 42 as shown.

Figure 10A:
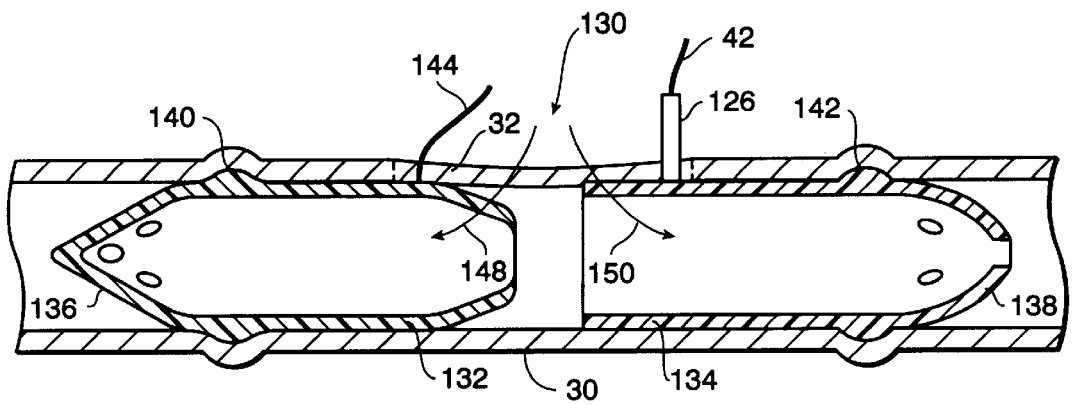
FIGS. 10A, 10B are simplified elevational views of an alternative two-piece embodiment of the invention, further depicting a sequence of steps taken by a surgeon to install the shunt at the anastomosis site.
Figure 10B:
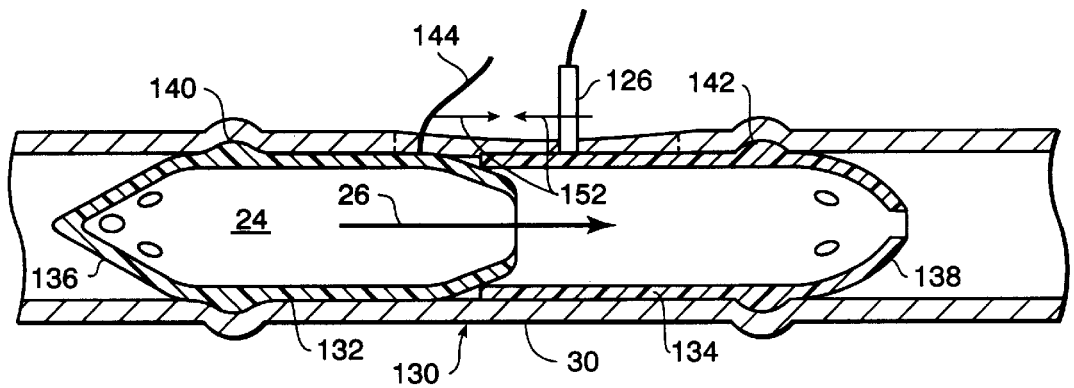

FIGS. 10A, 10B depict an alternative embodiment of a two piece shunt 130 which configuration facilitates the initial insertion of the shunt through the incision 32 and into the LAD 30. The shunt 130 is formed of two shortened central members 132, 134, wherein one central member, for example 132, has a slightly smaller diameter than the confronting central member, for example 134. The member 134 of larger diameter has a leading portion thereof somewhat hardened to facilitate the meshing and thus assembly of the two halves into the single piece shunt 130 (FIG. 10B). The shunt half formed of central member 132 includes a tapered end member 136 formed therewith similar to the more pointed end members 44, 46 of FIGS. 2–4, 6, 7. The shunt half formed of central member 134 includes a tapered end member 138 which resembles that of FIG. 9, but which could be otherwise. In this example, the annular ridges 140, 142 are shown as non-balloon types such as those of FIG. 3, but could comprise the balloon or other configurations of ridges of description herein. Filamentary strand 144 and an integral stub 126 are secured to respective central members 132, 134 respectively.

FIG. 10A depicts the separate insertion of each shunt half, where shunt half 132, 136 is inserted proximally in the LAD 30 using the strand 144 and forceps to urge the half in the direction shown by arrow 148. Then shunt half 134, 138 is inserted distally in the LAD 30 using an integral stub 126 and forceps to urge the half in the direction of arrow 150. Then as depicted in FIG. 10B, the two halves are manipulated to provide the single piece shunt 130 by gently pulling the strand 144 and stub 126, and thus the halves, towards each other as depicted by arrows 152, while guiding the halves with forceps until the halves are united. As may be seen, the distal half of the shunt 130 has the larger diameter such that the blood flow in the artery passes unobstructed from the smaller, inside diameter to the larger outside diameter in the joined region.

Figure 11A:
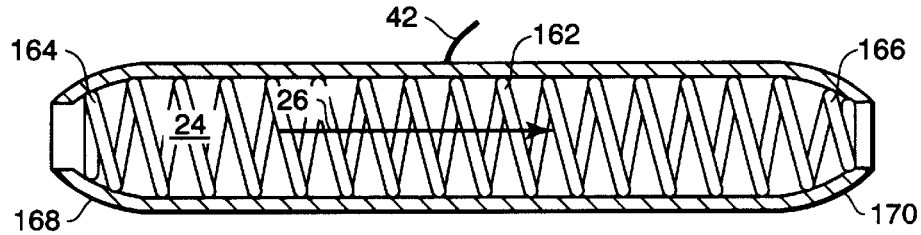
FIG. 11A is an elevational view, in cross-section, of a further alternative embodiment of the invention employing a very flexible coil coated with a flexible material such as silicon, latex, etc.
Figure 11B:
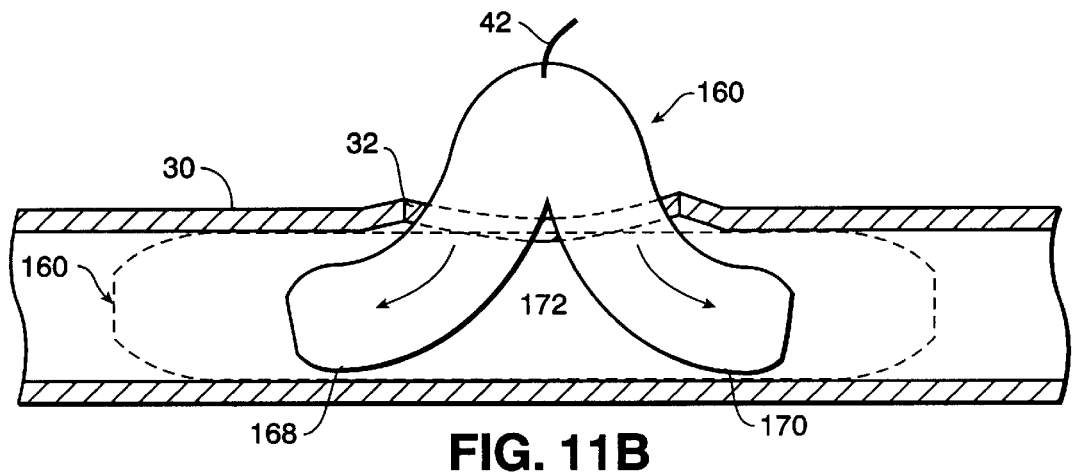
FIG. 11B is an elevational view illustrating a procedure for inserting the shunt of FIG. 11A in place in an artery via an incision.

FIGS. 11A, 11B depict a further alternative shunt 160 formed of a lightweight flexible coil 162 formed of, for example, a stainless steel filament. The spiral of the coil 162 preferably is tightened at the ends 164, 166 thereof to provide decreasing diameters and thus tapered end members 168, 170 for facilitating insertion in the artery 30. The coil 162 is coated with a flexible material such as, for example, silicon, to define an impervious tube having a lumen 24 therethrough. The resulting shunt is very flexible and is configured with an outside diameter which allows it to fit snugly within a blood vessel such as the LAD 30 while maintaining blood flow through the lumen. FIG. 11B depicts one manner of installing the shunt in the LAD 30, wherein the end members 168, 170 are pinched towards one another, passed through the incision 32, and then urged into respective proximal and distal portions of the LAD as shown by arrows 172, using the filamentary strand 42 and forceps. The coil shunt 160 is depicted in place within the LAD 30 in phantom line.

Figure 12A:
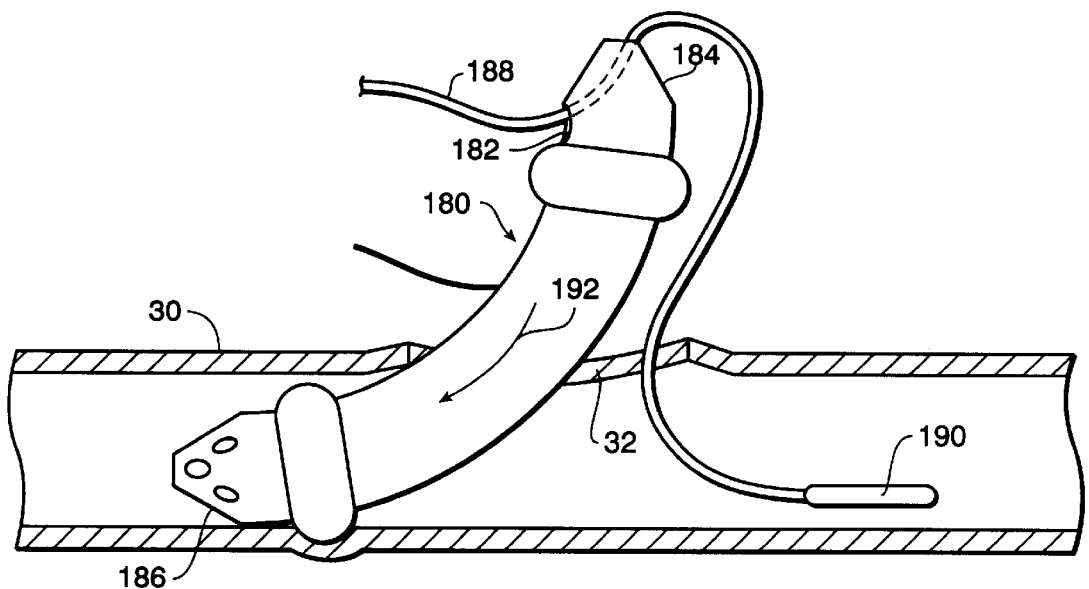
FIGS. 12A, 12B are elevational views, in partial cross-section, of a modified embodiment of the invention, illustrating a procedure for inserting the shunt in place in an artery via an incision.
Figure 12B:
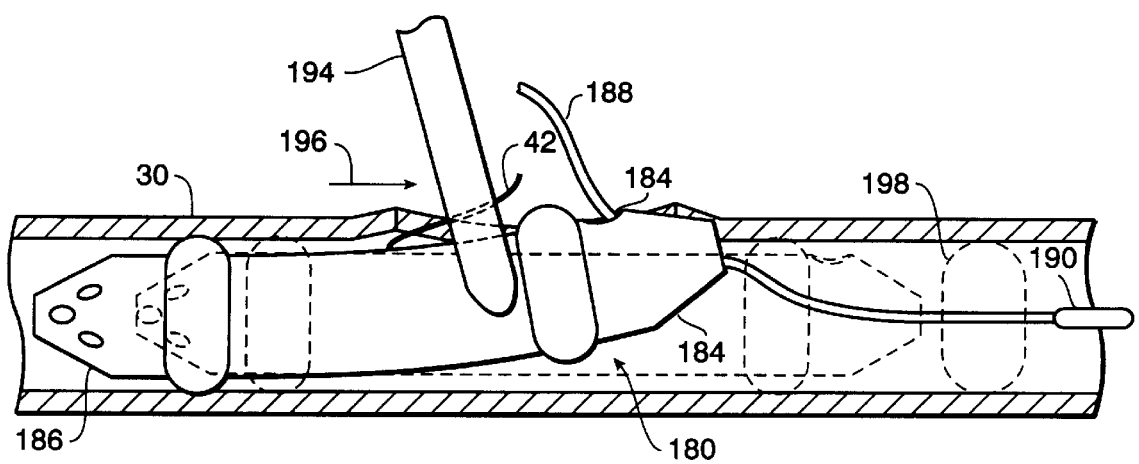

FIGS. 12A, 12B depict a further modification to a shunt or shunts of previous description, which modification lends itself to an alternative technique for insertion of a shunt 180 in place in a blood vessel such as the LAD 30. The shunt 180 is modified with a perforation 182 formed in the distal end member 184. The perforation 182 is adapted to receive a flexible guide wire 188 such as those used for catheters. The guide wire may include a typical helical coil 190 at the tip thereof or may include a balloon device as discussed below. Insertion of the shunt 180 is initiated as in FIG. 12A by inserting a proximal tapered end member 186 into the LAD 30 and urging the shunt as depicted by arrow 192 by gently pulling on the filamentary strand 42 while guiding and urging the shunt with forceps (not shown). The guide wire 188 is passed through the perforation 182 and thence through the incision 32 and distally into the LAD 30. As next depicted in FIG. 12B, the guide wire 188 then is used to guide the distal end member 184 into the LAD 30 while the shunt 180 is urged distally with forceps 194 and the strand 42, as depicted by arrow 196. After the shunt 180 is in place, as depicted in phantom line, the guide wire 188 is removed and the anastomosis construction can proceed. To prevent the guide wire 188 from being dislodged from its position distally in the LAD 30, a balloon device 198 typically employed with catheters may be employed at the end of the guide wire. Expansion of the balloon device 198 as depicted in phantom line secures the end of the guide wire 188 to prevent it from being dislodged while the shunt is being urged distally along the guide wire.

Figure 13A:
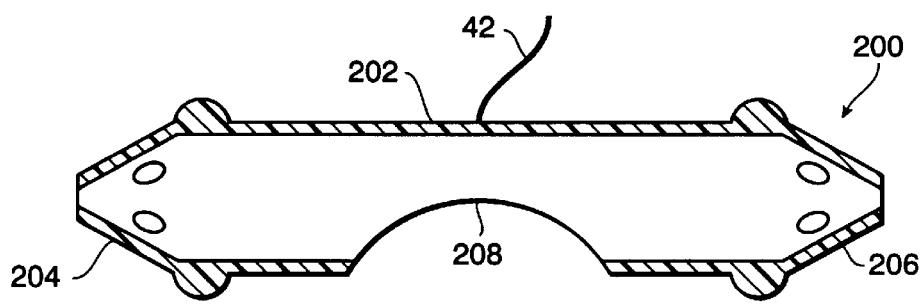
FIGS. 13A, 13B, 13C are elevational views, in cross-section, of a further modified embodiment of the invention, further illustrating a procedure for inserting the shunt in place in an artery via an incision.
Figure 13B:
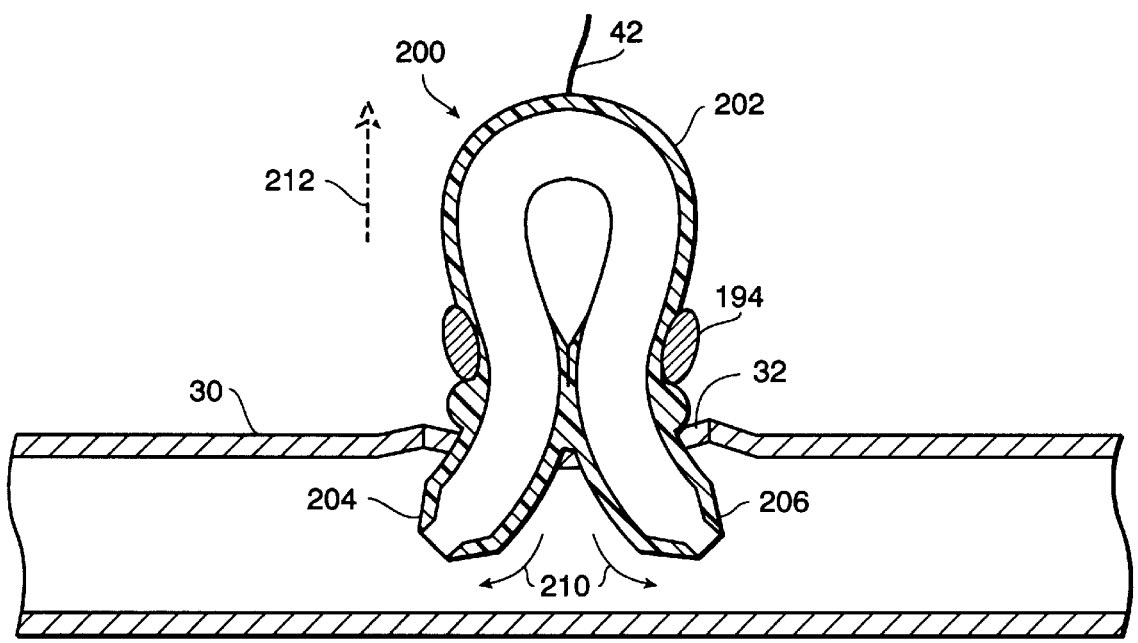
Figure 13C:
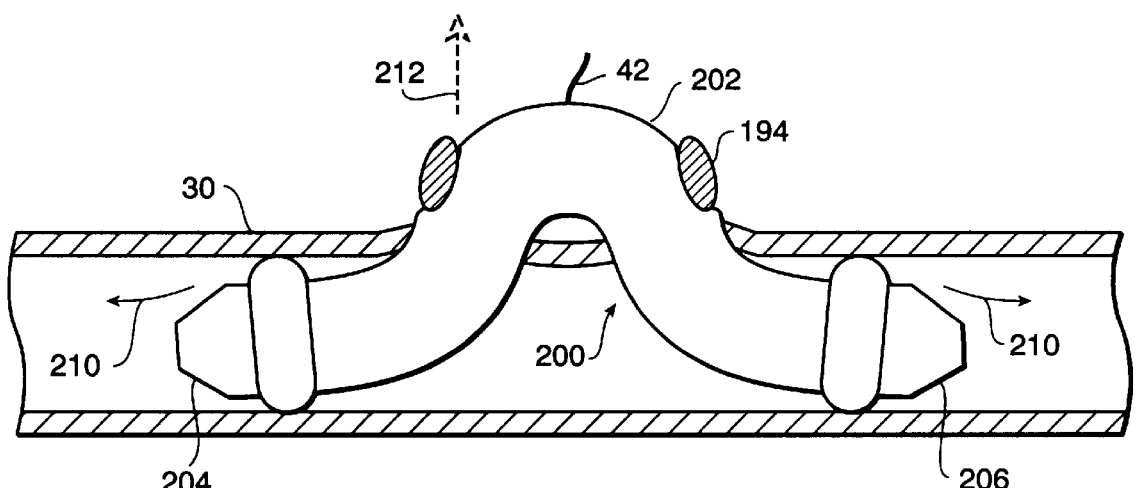

FIGS. 13A, 13B, 13C depict still another alternative embodiment of the invention and a preferred method of installation of a corresponding shunt 200 via the incision 32 of, for example, the LAD 30. The shunt 200 may be formed generally of one of the various shunt configurations of previous description with a central member 202 and tapered end members 204, 206. However, as depicted in FIG. 13A, the shunt 200 is modified by removing an arcuate portion from the central member 202 to define a necked-down section 208 along a substantial length of the central member 202, as shown. The arcuate portion which is removed may be of different lengths and/or depths into the central member, as desired. The necked-down section 208 enhances the bending flexibility of the shunt 200, which configuration thus lends itself to a preferred method of installation of the shunt 200.

To this end, referring to FIG. 13B, the shunt 200 may be folded at its middle in the direction of the necked-down section 208, and then pinched together as with the forceps 194 or other instrument of FIG. 12B, shown here in cross-section. The tapered end members 204, 206, in their pinched-together configuration, are inserted through the incision 32 and urged in respective proximal and distal directions in to the LAD 30, as depicted by arrows 210. Further gentle manipulation of the shunt 200 is made with the forceps 194 in successive stages until the shunt is in a position such as shown in FIG. 13C where each end member 204, 206 is fully aligned coaxially in the LAD 30. The shunt 200 then gently is reciprocated while being pushed down via the forceps into full alignment within the LAD 30, as shown in previous figures. Upon conclusion of the suturing process but prior to tightening the suture loops, the modified shunt 200 readily is removed by pulling gently on the filamentary strand 42 to raise the necked-out and thus flexible central member 202 sufficiently to enable the surgeon to grasp, and thus pinch together, the shunt via the forceps 194. Initial and subsequent movement of the shunt 200 also is depicted by FIGS. 13C, 13B, respectively, if the previous insertion steps of arrows 210 are reversed as depicted by arrow 212, shown in phantom line.

Figure 14A:
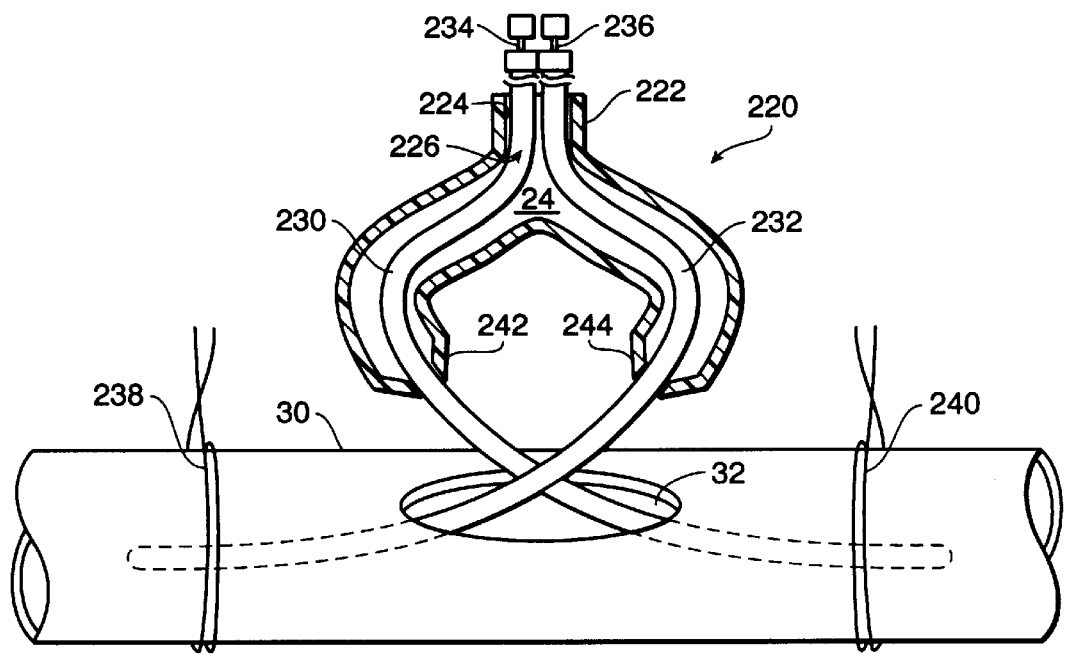
FIGS. 14A, 14B, 14C are elevational views, in partial cross-section, of a further alternative embodiment of the invention, further illustrating a procedure and associated implements for inserting the shunt in place.
Figure 14B:
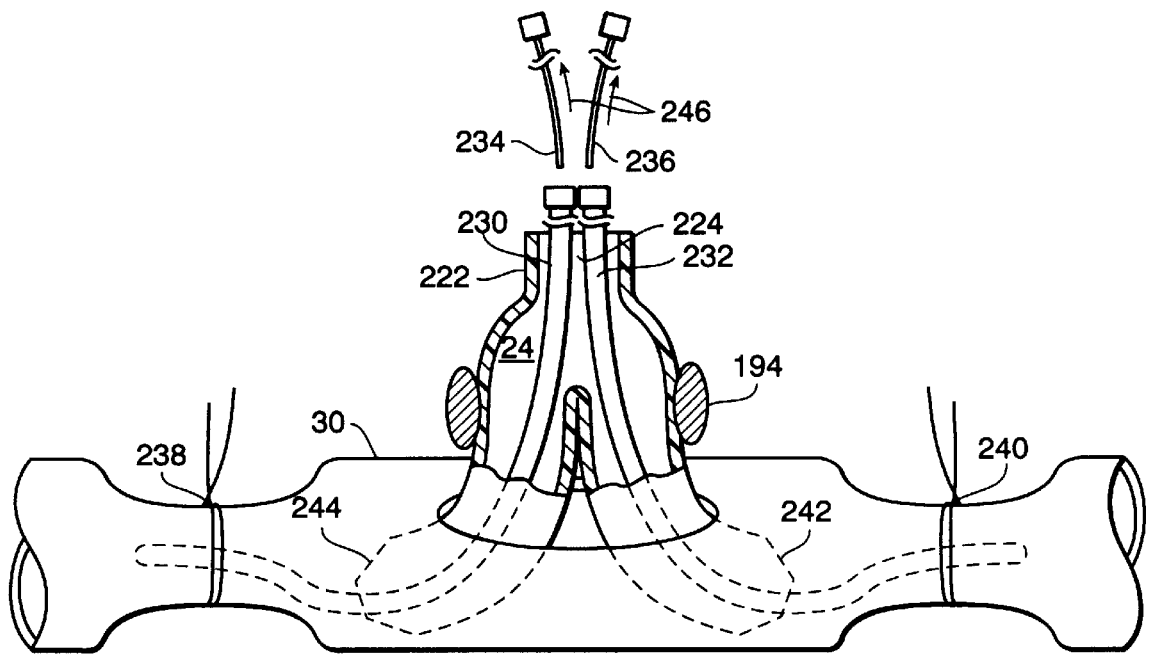
Figure 14C:
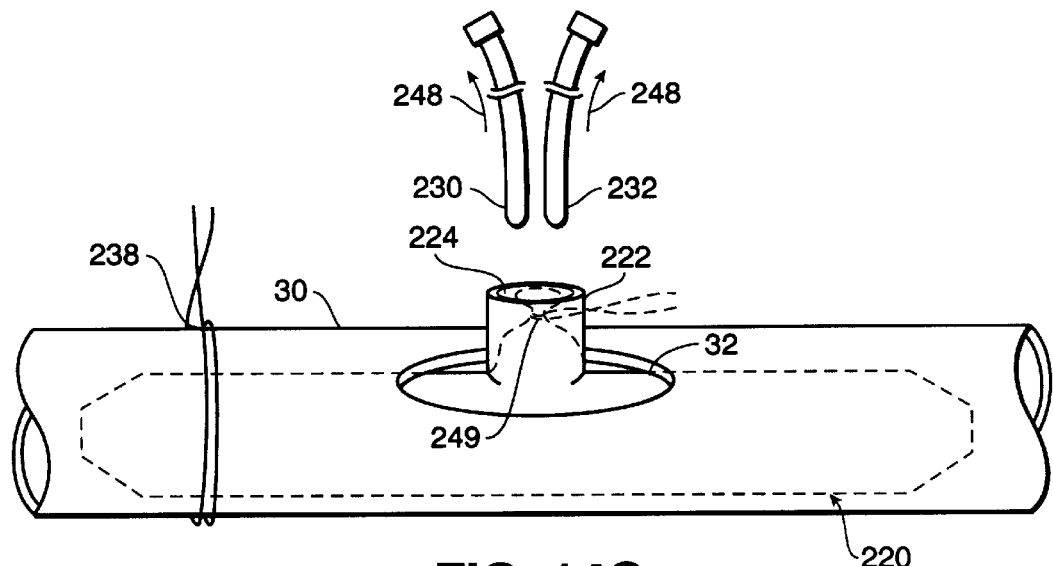

FIGS. 14A, 14B, 14C depict yet another alternative embodiment of the invention and another associated method of installation of a corresponding shunt 220 in place in an artery such as the LAD 30. The shunt 220, as in FIGS. 13A–13C, in general may comprise one of the shunt configurations of previous description formed of similar material. However, the shunt 220 is modified to include a shunt access member 222 which may be oval in cross-section to generally match the shape of the arteriotomy during the anastomosis construction and which provides an access lumen 224 in communication with the lumen 24 of the shunt 220. The configuration of the shunt 220 is illustrated in FIG. 14C installed in place in an artery such as the LAD 30. The shunt configuration employing the shunt access member 222 enables an installation procedure utilizing a pair of introducers 226, 228 which aid in guiding the shunt 220 into place in the LAD 30. The introducers are generally similar to dilators used in bypass procedures. In particular, the introducers 226, 228 each include a very flexible, or floppy, tube 230, 232 of for example a polymer material. A guide wire 234, 236 of selected firmer flexibility is threaded into respective floppy tubes 230, 232 to provide initial support for the tubes, to facilitate the shunt installation, described below.

FIG. 14A illustrates initial steps in the procedure of installing the shunt 220. A first step typically is to install proximal and distal snares 238, 240 loosely about the LAD 30 at locations proximal and distal to the arteriotomy or incision 32. The introducers 226, 228 are each threaded through the shunt access member 222, out through respective tapered end members 242, 244, and thence into the LAD 30 via respective distal and proximal apexes of the arteriotomy 32. As illustrated in FIG. 14A, the end of the introducer 226 is fed through the distal snare 240 while the end of the introducer 228 is fed through the proximal snare 238. FIG. 14A depicts the shunt 220 after initial steps of urging the shunt towards the incision 32 along the introducers 226, 228, wherein the tapered end members 242, 244 are forced to begin converging together as they are urged along the guiding introducers.

As shown in FIG. 14B, the snares 238, 240 are tightened before the installation procedure is continued, to secure the introducers in place in the LAD 30. The support wires 234, 236 then are removed from within the respective floppy tubes 230, 232 as depicted by arrows 246, to provide increased flexibility in rotating the shunt 220 while urging the end members 242, 244 into the LAD 30. Forceps 194 or other appropriate instruments are employed to aid in pinching the ends of the shunt 220 together to facilitate their entry through the arteriotomy, as shown in FIG. 14B. The procedure is continued until the shunt 220 is in place in the LAD 30, as depicted in partial phantom line in FIG. 14C. The snares 238, 240 are removed and the floppy tubes 230, 232 are removed from the shunt as shown by arrows 248. Alternatively, the snares can be retightened around the shunt as depicted by 238 in FIG. 14C to secure an adequate blood seal for the anastomosis. In one procedure, the shunt access member 222 is ligated with a suture 249, or with a filamentary strand previously secured about the member 222.

Alternatively, the shunt access member 222 may be replaced by an IMA supporting member such as that shown in FIG. 16. The distal end of the IMA then is slipped over the IMA supporting member which, together with the shunt 220, provides support for the anastomosis construction.

Although a pair of introducers are depicted in performing the installation procedure of FIGS. 14A–14C, a single introducer may be employed with an installation procedure generally similar to that described relative to FIGS. 12A–12B. That is, an introducer is threaded through the shunt access member 222, out one end member of the shunt and into the LAD 30. Then installation is accomplished by first inserting the free end of the shunt into the LAD opposite to the location of the end of the introducer, whereupon the introducer then is used along with forceps to finish the installation as in FIGS. 12A, 12B.

In addition, the ends of the single or dual introducers may include an inflatable balloon device such as balloon device 198 discussed relative to the guide wire 188 of FIG. 12B, to secure the introducer in place within the LAD 30. Thus, the snares 238, 240 may be dispensed with which reduces the arterial trauma which can occur from the pinching affect of the snare. Further, means other than a suture or strand may be employed to seal the shunt access member 222. For example, surgical clips or an expandable material such as the hydrogel material of previous mention, may be used.

Figure 15A:
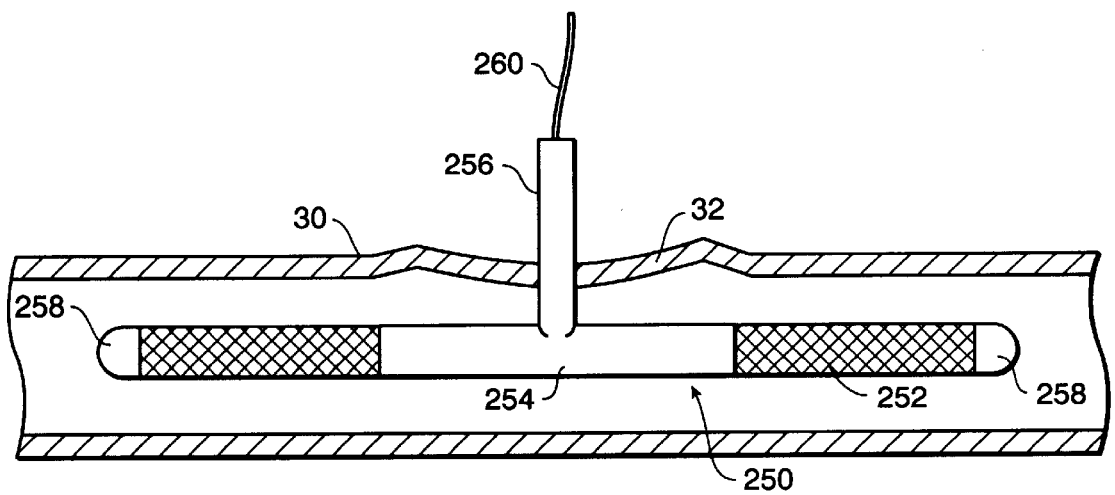
FIGS. 15A, 15B and 16A, 16B are elevational views of still other alternative embodiments of the invention employing a braided tube and a laminated foil structure, respectively.
Figure 15B:
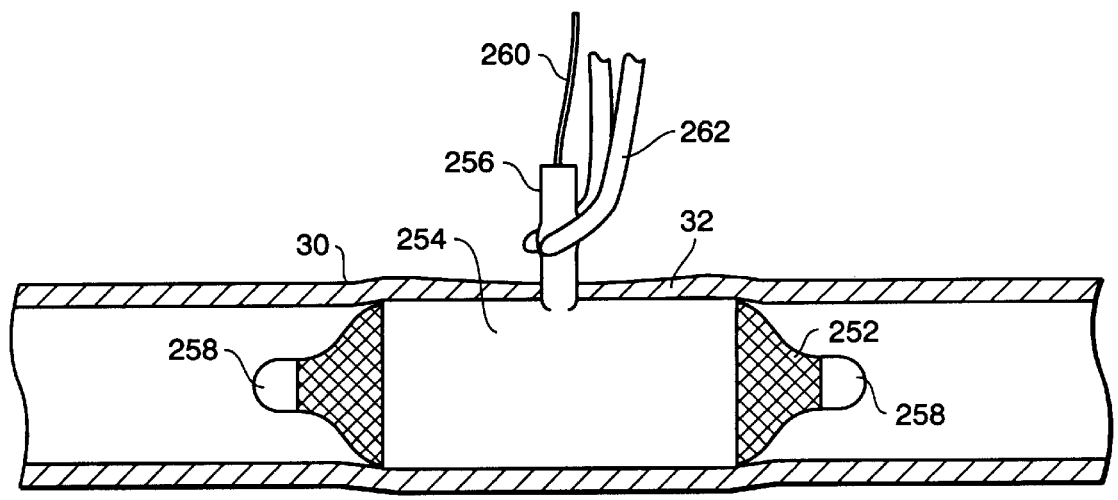

FIGS. 15A, 15B depict a further embodiment of the invention employing a braided tube 252 to form the central member and tapered end members of a shunt 250. A central portion 254 of the braided tube 252 is coated with an elastomer material to provide an impermeable membrane that stretches when the braided tube 252, that is, the shunt 250, is compressed axially. The remaining uncoated end portions of the braided tube 252 provide the tapered end members of previous description as well as the openings to allow the flow of blood through the shunt. A choker tube 256 is integrally secured to a mid point of the central portion 254 of the shunt. Atraumatic tips 258 of soft elastomer or plastic material are formed at the ends of the braided tube 252 to prevent damage to the artery during insertion. A thread 260 is secured to each end of the shunt and thence through the lumen of the central portion and out through the choker tube 256.

The shunt 250 is inserted through the arteriotomy or incision 32 by slipping first one end and then the other therethrough into the LAD 30, as depicted in FIG. 15A. As depicted in FIG. 15B, the shunt 250 is expanded radially outward to engage the interior wall of the LAD 30, by applying a pulling force to the thread 260 while holding the choker tube 256 to compress the braided tube 252 axially. The expanded central portion 254 spans, and thus occludes, the arteriotomy. The shunt is maintained in the expanded condition by pinching the choker tube 256 with locking forceps 262 or other pinching device, to lock the thread 260 therein.

Figure 16B:
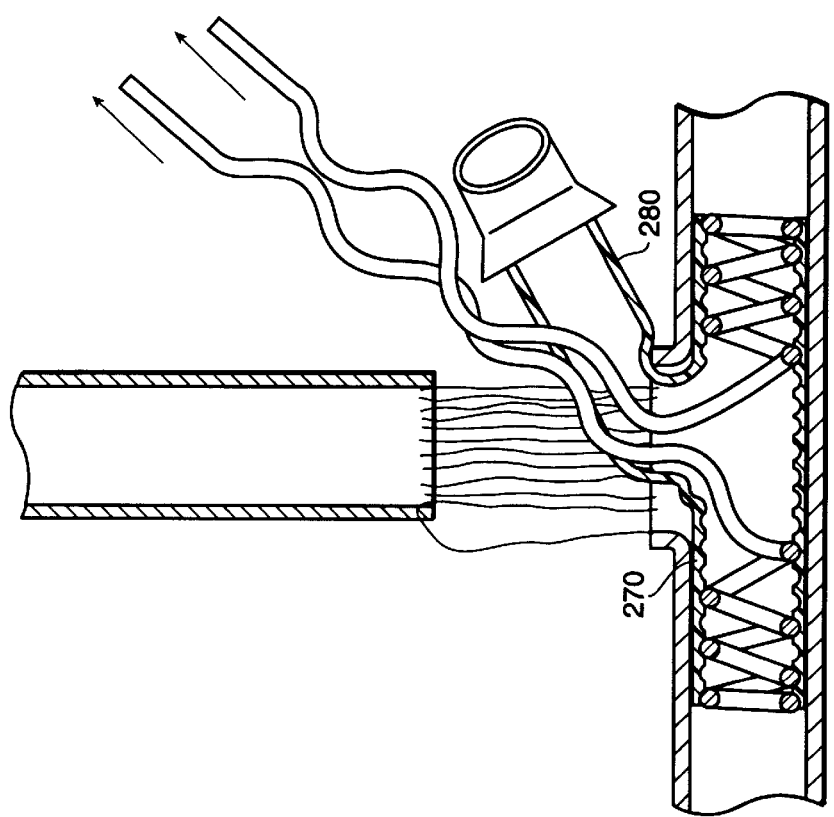
Figure 16A:
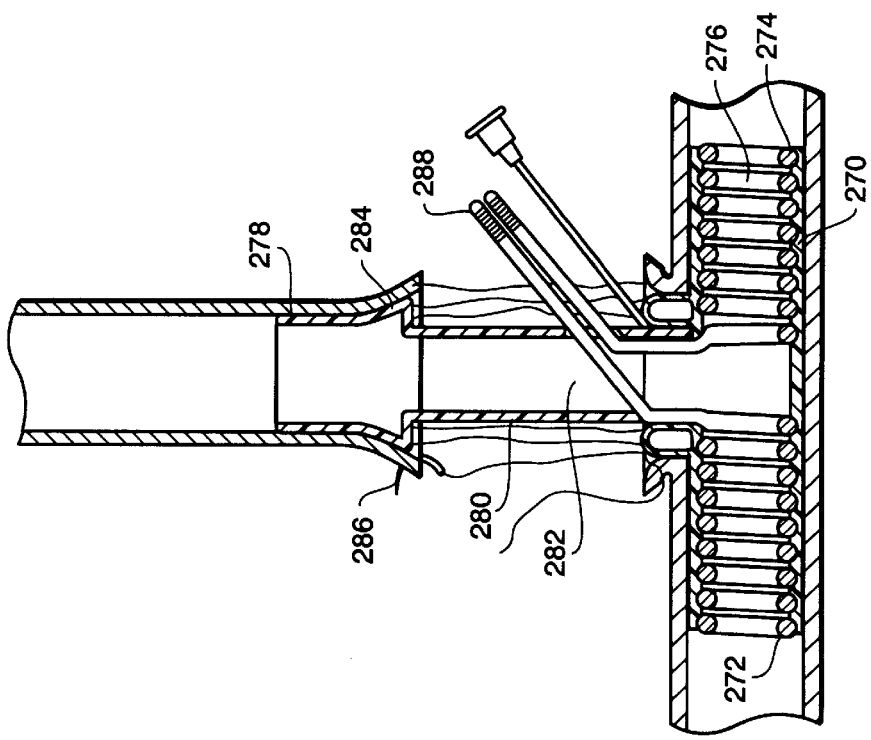

FIGS. 16A, 16B depict still a further embodiment of the invention wherein a coil shunt 270 is formed of a pair of coils 272, 274 which are laminated with an elastomer material to provide flexible tubular members about the coils. The elastomer material also is extend between the coils 272, 274 to define a tubular center member 276. The center member 276 is formed about and between the coils by means of, for example, a suitable molding process and may include, in the region of the anastomosis, an inflatable, generally oval shaped balloon device 278 which when inflated exposes the edges of the incision 32 to facilitate the suturing procedure. An IMA supporting member 280 formed of an elastomer material and having a lumen 282 therethrough, is molded at its distal end to the elastomer material extending between the coils 272, 274. The resulting IMA lumen 282 thus is in communication with the lumen 24 of the shunt 270 to allow the flow of blood from the IMA 38 to the LAD 30 if desired. However, the combined shunt structure, including the inflatable balloon device 278, maintain a dry anastomosis site. In addition, the IMA supporting member 280 may include at its proximal end an enlarged flange 284, formed of material such as hydrogel or an inflatable balloon, which exposes the distal end of the IMA 38 to further facilitate the suturing procedure. To illustrate, FIG. 16A depicts a suturing needle 286 used in a typical suturing procedure, wherein the procedure is aided by the exposure of the anastomosis by the IMA flange 284 and the balloon device 278 as depicted.

As show in FIGS. 16A, 16B, the proximate ends of the coils 242, 244 are accessible via coil removers 288 whereby the c oils may be unraveled independently from within the laminated elastomer material, FIG. 16B, to provide an enlarged lumen 24 or to facilitate the removal of the shunt 270.

It is understood that an IMA supporting tube, such as the tube 280 of FIGS. 16A, 16B, may be employed in the various shunt configurations of description herein if desired, and is not limited to use with the coil configuration as shown and described.

Figure 17:
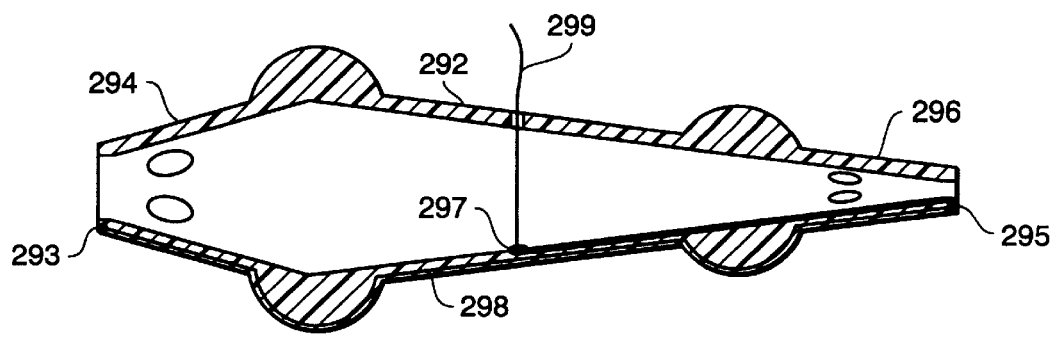
FIG. 17 is an elevational view, in cross-section, of an asymmetrical shunt configuration, further depicting a gum wrapper thread technique for facilitating shunt removal.

FIG. 17 depicts further alternative modifications to the various shunt configurations described herein, in accordance with the invention. For example, a central member 292 and associated tapered end members 294, 296 may be formed with slightly tapered geometry to define thus an asymmetrical shunt configuration matching the typical decreasing diameter of a coronary artery in the distal direction. In addition, a shunt may include a ôgum wrapper openingö means for splitting the shunt, either axially along its length of circumferentially, to enhance the collapse of the shunts diameter to facilitate its removal. To this end, in FIG. 17, a thread 298, flexible wire, etc., is embedded within the wall of the shunt, preferably at least along the central member 292. The thread 298 may extend from a point 293 along the length of the shunt to a point 295, and thence in a loose loop to a tear patch 297. The thread then extends from the shunt as depicted at 299 through, for example, a suitable opening in the diametrically opposed wall of the central member 292. Thus the thread 298 is used as the means for aiding the insertion of the shunt where gentle pulling does not tear the patch 297 to initiate the splitting action. When the shunt is to be removed, forceps or other appropriate instruments are placed against the shunt and a greater pulling force is applied to tear the patch 297 and cause the thread 298 to slice through the shunt wall much in the manner that the thin ribbon in a gum pack severs the enclosing plastic wrapper to expose the gum.

Figure 18:
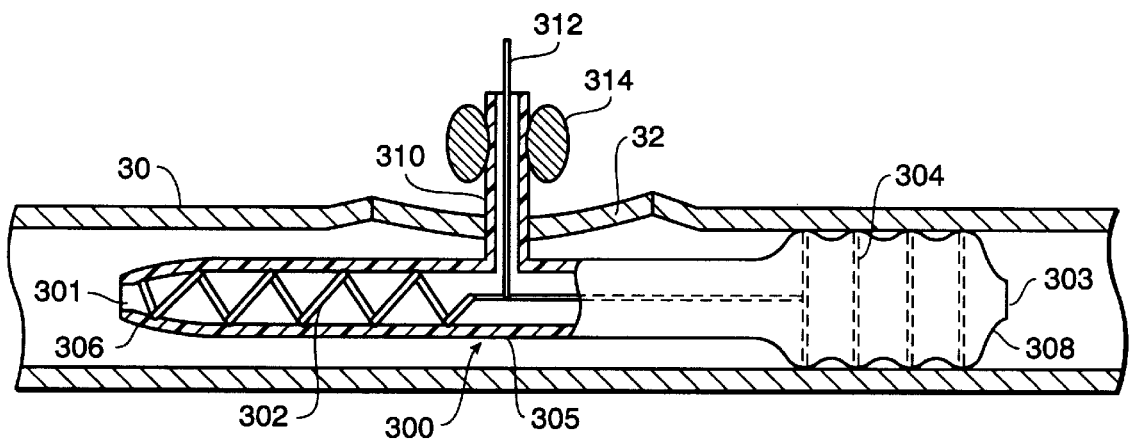
FIG. 18 is an elevational view of yet another alternative embodiment of the invention employing an expanding spring structure.

FIG. 18 depicts a further alternative embodiment of the invention, wherein a further coil structure is employed in a shunt 300. More particularly, thin, flexible wire springs or coils 302, 304 are laminated with a coating of a flexible elastomer material, generally as previous depicted in FIG. 16A, 16B, to form an impervious central member 305 and generally tapered end members 306, 308. The end members are formed with openings 301, 303. A choker tube 310 is formed with a wall of the central member 304 at generally a midpoint and extends generally normal therefrom. Threads are secured to respective facing ends of the coils 302, 304, are passed through the choker tube 310 as divided threads and extend from the tube as a united thread 312. As depicted in solid, a pulling force applied to the thread 312 while the choker tube 310 is held axially stretches the coils (herein only coil 302 and laminated coating is shown in a stretched condition). A locking forceps 314 used to pinch the choker tube 310 against the thread 312 maintains the coils and thus the shunt in the extended condition. The small diameter of the shunt 300 allows ready insertion in the artery. Once in place, the forceps 314 are removed and the coils 302, 304 return to their natural axially compact state (herein shown by the coil 304 and laminated coating, in phantom line). As may be seen, when the coils 302, 304 return to their natural state, the diameters of the shunt 300 at either end expand radially outward to provide snug engagement of the elastomer coating with the interior walls of the LAD 30 proximal and distal to the anastomosis site.

Figure 19:
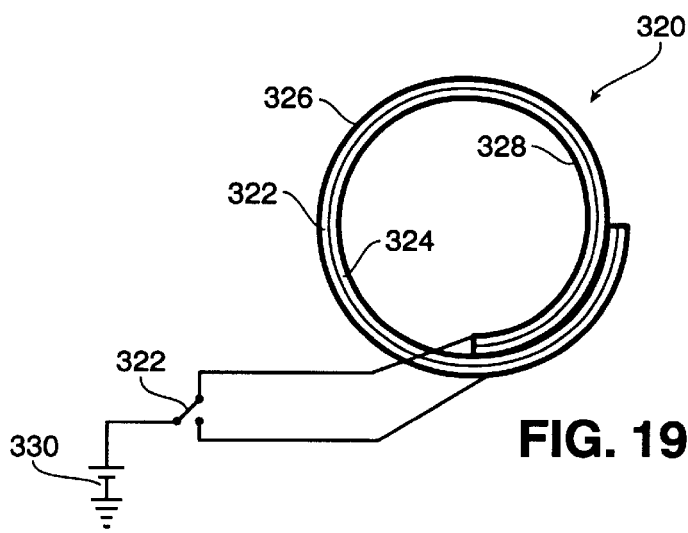
FIG. 19 is a cross-sectional view of another alternative embodiment of the invention.

FIG. 19 depicts a further alternative embodiment of an expandable shunt 320 wherein a cylindrical unfolding spiral is formed of two bonded sheets 322, 324 of, for example, a nickel-titanium alloy material having an inherent shape-memory property. One sheet, for example 324, is annealed in the shape of a tightly curled cylinder, while the other sheet, for example 322, is annealed as a flat or less curled sheet. A heating coil 326, 328 is bonded to respective sheets 322, 324. The shunt 320 is formed of the bonded sheets rolled into a spiral cylinder of a diameter corresponding to the desired diameter in use. Since the shunt 320 is expandable through most sizes of arteries, the initial diameter of the shunt may be made smaller than the diameter of the smallest arteries. Application of a small electrical current for a short duration to the coil 328 bonded to the tightly curled sheet 324 via, for example, a voltage source 330 and a switch 332, causes the sheet to contract, facilitating the insertion of the shunt 320 in the artery 30. Upon insertion of the shunt, another small electrical current is applied for a short duration to the coil 326 of the sheet 322 which is annealed while flat or less curled, causing the cylindrical spiral to unfold to expand the diameter of the shunt. When contraction of the shunt 320 is desired as when the shunt is to be removed, the current is applied to the coil 328 which causes the cylindrical spiral to contract radially inward.

Although the invention has been described herein relative to specific embodiments and modifications, various additional features and combinations of those specifically described will be apparent from the description and drawings. Thus the scope of the invention is defined by the following claims and their equivalents.

What is claimed is:

1. A distal perfusion device for maintaining blood flow in a blood vessel to prevent ischemia while further maintaining a dry anastomosis site to facilitate the suturing procedure during the construction of an anastomosis comprising:

a flexible central member having and outer diameter and having a centrally disposed lumen for the passage of fluid and a pair of pointed and tapered end members formed at proximal and distal extremities of the central member having integrally formed now-inflatable annular ridges with pre-selected outer diameters greater than the outer diameter of said central member and at least one perforation for the passage of fluid therethrough.

2. The distal perfusion device of claim 1 further comprised of a filamentary strand attached to the central member.

3. The distal perfusion device of claim 2 wherein said strand comprises two diverging strands attached to the central member at spaced-apart points to facilitate insertion of the device into the vessel.

4. The distal perfusion device of claim 2 further comprising a choker tube or stub.

5. The distal perfusion device of claim 4 wherein the choker tube or stub is integrally secured to the central member by said filamentary strand wherein said filamentary strand extends through said choker tube.

6. The distal perfusion device of claim 2 wherein a portion of said strand is embedded within the wall and along the length of the central members such that when a pulling force is applied to said strand, the central member is caused to separate along its length.

7. The distal perfusion device of claim 1 wherein the relative geometry of the end members is asymmetrical.

8. The distal perfusion device of claim 1 wherein the end members are each tapered to a smaller diameter from a point of attachment to the central member.

9. The distal perfusion device of claim 1 wherein the central member is comprised of a flexible coil.

10. The distal perfusion device of claim 9 wherein the device is comprised of a material selected from the group consisting of silicone, an elastomer material, a polymer material, and a polymer elastomer.

11. The distal perfusion device of claim 1 wherein the apex of each said tapered end member is closed.

12. The distal perfusion device of claim 1 wherein said central member comprises an expandable polymeric spiral.

13. The distal perfusion device of claim 1 wherein said central member comprises a necked-down section along a substantial portion of the length of the central member.

14. The distal perfusion device of claim 1 wherein each said tapered end member comprises one perforation generally coincident with the apex of said end member.

15. A method of employing a perfusion device at an anastomosis site in a vessel, comprising the steps of:

inserting a first tapered end member of the perfusion device through an arteriotomy, advancing the first end member into the vessel beyond the apex of the arteriotomy wherein the first end member has at least one annular ridge with a preselected diameter to engage the interior of the vessel, inserting a second tapered end member beyond the opposite apex of the arteriotomy such that the distal perfusion device is positioned coaxially within the vessel maintaining blood flow distally through the vessel while the perfusion device is in place.

16. The method of claim 15 further comprising the step of centering the perfusion device relative to the apexes of the arteriotomy such that the perfusion device spans the arteriotomy.

17. The method of claim 16 further comprising the step of:

removing the device with a thread attached to the central member.

18. The method of claim 15 wherein the perfusion device is flexed at a point along the central member to facilitate placing the second tapered end member into the arteriotomy and into place in the vessel.

19. The method of claim 15 further comprising sealing blood flow from the anastomosis using a suture surrounding the perfusion device and the vessel.

20. Apparatus for maintaining blood flow in a blood vessel to prevent ischemia while further maintaining a dry anastomosis site to facilitate the suturing procedure during the construction of an anastomosis of said vessel with a second vessel, comprising:

a selection of distinctly sized distal perfusion devices, each said device comprising a flexible central member having an outer diameter and having a centrally disposed lumen and a pair of pointed and tapered end members formed at the proximal and distal extremities of the central member, wherein said end members of each of said devices has integrally formed now-inflatable annular ridges with preselected outer diameters greater than the outer diameter of said central member and at least one perforation for the passage of fluid therethrough.

21. The apparatus of claim 20 wherein said preselected diameters of said integrally formed annular ridges differ among said selection of distinctly sized distal perfusion devices.

22. The apparatus of claim 21 wherein the relative geometry of the end members is asymmetrical.

* * * * *

UNITED STATES PATENT AND TRADEMARK OFFICE
CERTIFICATE OF CORRECTION

| | | |
|---|---|---|
| PATENT NO. | : | 5,769,870 |
| DATED | : | June 23, 1998 |
| INVENTOR(S) | : | Amr Salahieh, et al. |

It is certified that error appears in the above-identified patent and that said Letters Patent is hereby corrected as shown below:

In claim 1, column 15, line 8, delete "and" and insert therefor --an--.

In claim 1, column 15, line 12, delete "now-inflatable" and insert therefor --non-inflatable--.

In claim 20, column 16, lines 41-42, delete "now-inflatable" and insert therefor --non-inflatable--.

Signed and Sealed this

Sixteenth Day of March, 1999

Attest:

Q. TODD DICKINSON

*Attesting Officer*  *Acting Commissioner of Patents and Trademarks*